United States Patent
House et al.

(10) Patent No.: US 8,906,087 B2
(45) Date of Patent: Dec. 9, 2014

(54) METHOD OF MAKING IMPLANTABLE DEVICES WITH REDUCED NEEDLE PUNCTURE SITE LEAKAGE

(75) Inventors: Wayne D. House, Flagstaff, AZ (US); Edward H. Cully, Flagstaff, AZ (US); Daniel B. Pond, Flagstaff, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 0 days.

(21) Appl. No.: 13/250,656

(22) Filed: Sep. 30, 2011

(65) Prior Publication Data

US 2012/0058249 A1 Mar. 8, 2012

Related U.S. Application Data

(62) Division of application No. 10/999,276, filed on Nov. 29, 2004, now Pat. No. 8,029,563.

(51) Int. Cl.
*A61F 2/06* (2013.01)

(52) U.S. Cl.
USPC ...................................................... 623/1.44

(58) Field of Classification Search
USPC ............. 623/1.1, 1.11, 1.13, 1.14, 1.18, 1.22, 623/1.23, 1.27, 1.32, 1.39, 1.4, 1.44–1.54
See application file for complete search history.

(56) References Cited

U.S. PATENT DOCUMENTS

| | | |
|---|---|---|
| 3,425,418 A | 2/1969 | Chvapil et al. |
| 3,814,137 A | 6/1974 | Martinez |
| 3,914,802 A | 10/1975 | Reick |
| 4,133,927 A | 1/1979 | Tomoda et al. |
| 4,193,138 A | 3/1980 | Okita |
| 4,208,745 A | 6/1980 | Okita |
| 4,229,838 A | 10/1980 | Mano |
| 4,279,245 A | 7/1981 | Takagi et al. |
| 4,283,448 A | 8/1981 | Bowman |
| 4,304,010 A | 12/1981 | Mano |

(Continued)

FOREIGN PATENT DOCUMENTS

| | | |
|---|---|---|
| EP | 117072 | 8/1984 |
| EP | 256748 | 2/1988 |

(Continued)

OTHER PUBLICATIONS

Berman M, Pearce W, et al. The use of Gore-Tex® E-PTFE bonded to silicone rubber as an alloplastic implant material. Laryngoscope 1986; v96 n5: 480-483.

(Continued)

*Primary Examiner* — Howie Matthews
(74) *Attorney, Agent, or Firm* — Wayne House

(57) ABSTRACT

A prosthetic implantable device that offers a reduction in fluid loss when the device is punctured, such as by a dialysis needle or suture needle, and the needle is subsequently removed. The device may be made to be thin and flexible, and with longitudinal stretch, in order that it also offers good handling and kink resistance to a surgeon. While the device is preferably of tubular form, flat sheets or other forms may also be made. The device includes inner and outer layers of a porous material having a microstructure of nodes interconnected by bent fibrils, and having void spaces between adjacent bent fibrils. The inner and outer layers are joined by an elastomeric adhesive that may interpenetrate the void spaces of the adjacent surfaces of the inner and outer layers, that is, the inner surface of the outer layer and the outer surface of the inner layer.

2 Claims, 8 Drawing Sheets

(56) References Cited

U.S. PATENT DOCUMENTS

| | | |
|---|---|---|
| 4,321,711 A | 3/1982 | Mano |
| 4,347,204 A | 8/1982 | Takagi et al. |
| 4,416,028 A | 11/1983 | Eriksson et al. |
| 4,443,511 A | 4/1984 | Worden et al. |
| RE31,618 E | 7/1984 | Mano et al. |
| 4,474,630 A | 10/1984 | Planck et al. |
| 4,478,898 A | 10/1984 | Kato |
| 4,550,447 A | 11/1985 | Seiler, Jr. et al. |
| 4,604,762 A | 8/1986 | Robinson |
| 4,613,544 A | 9/1986 | Burleigh |
| 4,619,641 A | 10/1986 | Schanzer |
| 4,657,544 A | 4/1987 | Pinchuk |
| 4,687,482 A | 8/1987 | Hanson |
| 4,692,369 A | 9/1987 | Nomi |
| 4,731,073 A | 3/1988 | Robinson |
| 4,739,013 A | 4/1988 | Pinchuk |
| 4,743,252 A | 5/1988 | Martin, Jr. et al. |
| 4,743,480 A | 5/1988 | Campbell et al. |
| 4,759,757 A | 7/1988 | Pinchuk |
| 4,787,921 A | 11/1988 | Shibata et al. |
| 4,804,381 A | 2/1989 | Turina et al. |
| 4,810,749 A | 3/1989 | Pinchuk |
| 4,816,339 A | 3/1989 | Tu et al. |
| 4,850,999 A | 7/1989 | Planck |
| 4,857,069 A | 8/1989 | Kira |
| 4,871,361 A | 10/1989 | Kira |
| 4,875,468 A | 10/1989 | Krauter et al. |
| 4,877,661 A | 10/1989 | House et al. |
| 4,882,113 A | 11/1989 | Tu et al. |
| 4,891,407 A | 1/1990 | Mitchell |
| 4,921,495 A | 5/1990 | Kira |
| 4,932,964 A | 6/1990 | Bittmann et al. |
| 4,945,125 A | 7/1990 | Dillon et al. |
| 4,955,899 A | 9/1990 | Della Corna et al. |
| 4,969,896 A | 11/1990 | Shors |
| 4,973,609 A | 11/1990 | Browne |
| 5,024,671 A | 6/1991 | Tu et al. |
| 5,061,276 A | 10/1991 | Tu et al. |
| 5,064,593 A | 11/1991 | Tamaru et al. |
| 5,066,683 A | 11/1991 | Dillon et al. |
| 5,071,609 A | 12/1991 | Tu et al. |
| 5,084,065 A | 1/1992 | Weldon et al. |
| 5,100,422 A | 3/1992 | Berguer et al. |
| 5,104,400 A | 4/1992 | Berguer et al. |
| 5,116,360 A | 5/1992 | Pinchuk et al. |
| 5,123,151 A | 6/1992 | Uehara et al. |
| 5,123,917 A | 6/1992 | Lee |
| 5,128,092 A | 7/1992 | Asaumi et al. |
| 5,133,742 A | 7/1992 | Pinchuk |
| 5,152,782 A | 10/1992 | Kowligi et al. |
| 5,192,310 A | 3/1993 | Herweck et al. |
| 5,217,797 A | 6/1993 | Knox et al. |
| 5,229,431 A | 7/1993 | Pinchuk |
| 5,290,271 A | 3/1994 | Jernberg |
| 5,320,888 A | 6/1994 | Stevens |
| 5,354,329 A | 10/1994 | Whalen |
| 5,358,516 A | 10/1994 | Myers et al. |
| 5,370,681 A | 12/1994 | Herweck et al. |
| 5,453,235 A | 9/1995 | Calcote et al. |
| 5,466,252 A | 11/1995 | Soukup et al. |
| 5,476,589 A | 12/1995 | Bacino |
| 5,527,353 A | 6/1996 | Schmitt |
| 5,529,820 A | 6/1996 | Nomi et al. |
| 5,549,664 A | 8/1996 | Hirata et al. |
| 5,556,426 A | 9/1996 | Popadiuk et al. |
| 5,584,876 A | 12/1996 | Bruchman et al. |
| 5,607,478 A | 3/1997 | Lentz et al. |
| 5,609,624 A | 3/1997 | Kalis |
| 5,620,763 A | 4/1997 | House et al. |
| 5,628,782 A | 5/1997 | Myers et al. |
| 5,628,788 A | 5/1997 | Pinchuk |
| 5,641,373 A | 6/1997 | Shannon et al. |
| 5,647,400 A | 7/1997 | Jani et al. |
| 5,665,114 A | 9/1997 | Weadock et al. |
| 5,700,287 A | 12/1997 | Myers et al. |
| 5,716,395 A | 2/1998 | Myers et al. |
| 5,716,660 A | 2/1998 | Weadock et al. |
| 5,718,973 A | 2/1998 | Lewis et al. |
| 5,735,892 A | 4/1998 | Myers et al. |
| 5,747,128 A | 5/1998 | Campbell et al. |
| 5,749,880 A | 5/1998 | Banas et al. |
| 5,788,626 A | 8/1998 | Thompson |
| 5,789,047 A | 8/1998 | Sasaki et al. |
| 5,800,510 A | 9/1998 | Schmitt |
| 5,800,512 A | 9/1998 | Lentz et al. |
| 5,824,050 A | 10/1998 | Karwoski et al. |
| 5,840,240 A | 11/1998 | Stenoien |
| 5,843,173 A | 12/1998 | Shannon et al. |
| 5,851,229 A | 12/1998 | Lentz et al. |
| 5,851,230 A | 12/1998 | Lentz et al. |
| 5,866,217 A | 2/1999 | Stenoien et al. |
| 5,897,587 A | 4/1999 | Martakos et al. |
| 5,904,967 A | 5/1999 | Ezaki et al. |
| 5,910,168 A | 6/1999 | Myers et al. |
| 5,931,865 A | 8/1999 | Silverman et al. |
| 5,976,192 A | 11/1999 | McIntyre et al. |
| 6,001,125 A | 12/1999 | Golds et al. |
| 6,016,848 A | 1/2000 | Egres, Jr. |
| 6,027,779 A | 2/2000 | Campbell et al. |
| 6,036,724 A | 3/2000 | Lentz et al. |
| 6,039,755 A | 3/2000 | Edwin et al. |
| 6,042,666 A | 3/2000 | Karwoski et al. |
| 6,053,939 A | 4/2000 | Okuda et al. |
| 6,056,970 A | 5/2000 | Greenawalt et al. |
| 6,080,198 A | 6/2000 | Lentz et al. |
| 6,099,557 A | 8/2000 | Schmitt |
| 6,159,565 A | 12/2000 | Campbell et al. |
| 6,165,211 A | 12/2000 | Thompson |
| 6,203,735 B1 | 3/2001 | Edwin et al. |
| 6,261,257 B1 | 7/2001 | Uflacker et al. |
| 6,267,834 B1 | 7/2001 | Shannon et al. |
| 6,287,337 B1 | 9/2001 | Martakos et al. |
| 6,319,279 B1 | 11/2001 | Shannon et al. |
| 6,328,762 B1 | 12/2001 | Anderson et al. |
| 6,338,904 B1 | 1/2002 | Patnaik et al. |
| 6,368,347 B1 | 4/2002 | Maini et al. |
| 6,416,537 B1 | 7/2002 | Martakos et al. |
| 6,428,571 B1 | 8/2002 | Lentz et al. |
| 6,517,571 B1 | 2/2003 | Brauker et al. |
| 6,517,858 B1 | 2/2003 | LeMoel et al. |
| 6,521,284 B1 | 2/2003 | Parsons et al. |
| 6,534,084 B1 | 3/2003 | Vyakarnam et al. |
| 6,547,820 B1 | 4/2003 | Staudenmeier |
| 6,589,468 B1 | 7/2003 | Schmitt |
| 6,712,919 B2 | 3/2004 | Ruefer et al. |
| 6,716,239 B2 | 4/2004 | Sowinski et al. |
| 6,719,783 B2 | 4/2004 | Lentz et al. |
| 6,790,226 B2 | 9/2004 | Edwin et al. |
| 6,814,753 B2 | 11/2004 | Schmitt |
| 6,827,737 B2 | 12/2004 | Hill et al. |
| 6,863,686 B2 | 3/2005 | Shannon et al. |
| 6,926,735 B2 | 8/2005 | Henderson |
| 6,939,377 B2 | 9/2005 | Jayaraman et al. |
| 7,056,336 B2 | 6/2006 | Armstrong et al. |
| 7,056,387 B2 | 6/2006 | van der Steur |
| 7,108,701 B2 | 9/2006 | Evens et al. |
| 7,147,617 B2 | 12/2006 | Henderson et al. |
| 7,244,271 B2 | 7/2007 | Lentz et al. |
| 7,297,158 B2 | 11/2007 | Jensen |
| 7,351,257 B2 | 4/2008 | Kaldany |
| 7,396,363 B2 | 7/2008 | Frid |
| 7,452,374 B2 | 11/2008 | Hain et al. |
| 7,510,571 B2 | 3/2009 | Spiridigliozzi et al. |
| 7,553,326 B2 | 6/2009 | Sweet et al. |
| 7,560,006 B2 | 7/2009 | Rakos et al. |
| 2003/0004559 A1 | 1/2003 | Lentz et al. |
| 2003/0027775 A1 | 2/2003 | Wallace |
| 2003/0060871 A1 | 3/2003 | Hill et al. |
| 2003/0100859 A1 | 5/2003 | Henderson et al. |
| 2003/0139806 A1 | 7/2003 | Haverkost et al. |
| 2003/0153983 A1 | 8/2003 | Miller et al. |
| 2004/0024442 A1 | 2/2004 | Sowinski et al. |
| 2004/0033364 A1 | 2/2004 | Spiridigliozzi et al. |
| 2004/0049264 A1 | 3/2004 | Sowinski et al. |

(56) References Cited

U.S. PATENT DOCUMENTS

| | | |
|---|---|---|
| 2004/0054406 A1 | 3/2004 | Dubson et al. |
| 2004/0122507 A1 | 6/2004 | Henderson |
| 2004/0182511 A1 | 9/2004 | Rakos et al. |
| 2004/0193242 A1 | 9/2004 | Lentz et al. |
| 2004/0215337 A1 | 10/2004 | Hain et al. |
| 2004/0265352 A1 | 12/2004 | Kaldany |
| 2005/0137677 A1 | 6/2005 | Rush |
| 2005/0187607 A1 | 8/2005 | Akhtar et al. |
| 2005/0249776 A1 | 11/2005 | Chen et al. |
| 2006/0041318 A1 | 2/2006 | Shannon |
| 2007/0116736 A1 | 5/2007 | Argentieri et al. |
| 2007/0276474 A1 | 11/2007 | Llanos et al. |
| 2007/0293808 A1 | 12/2007 | Williams et al. |
| 2008/0027534 A1 | 1/2008 | Edwin et al. |
| 2008/0195079 A1 | 8/2008 | Moore et al. |
| 2009/0270973 A1 | 10/2009 | Chen et al. |

FOREIGN PATENT DOCUMENTS

| | | |
|---|---|---|
| EP | 266035 | 5/1988 |
| EP | 0 492 481 | 7/1992 |
| EP | 656196 | 6/1995 |
| EP | 1131113 | 2/2000 |
| EP | 1101458 | 5/2001 |
| EP | 1925270 | 5/2008 |
| GB | 2033232 | 10/1978 |
| GB | 1590101 | 5/1981 |
| GB | 2222954 | 3/1990 |
| JP | 5474514 | 6/1979 |
| JP | 5925725 | 9/1984 |
| JP | 5176947 | 7/1993 |
| JP | 6343688 | 12/1994 |
| JP | 8238263 | 9/1996 |
| JP | 2739420 | 4/1998 |
| JP | 11099163 | 4/1999 |
| WO | 95/10247 | 4/1995 |
| WO | 98/26731 | 6/1998 |
| WO | 01/21107 | 3/2001 |
| WO | 01/32382 | 5/2001 |
| WO | 01/67991 | 9/2001 |
| WO | 03/015837 | 2/2003 |
| WO | 03/084440 | 10/2003 |
| WO | 2004/000375 | 12/2003 |
| WO | 2004/060209 | 7/2004 |
| WO | 2004/096307 | 11/2004 |
| WO | 2006/007214 | 1/2006 |
| WO | 2006/026725 | 3/2006 |
| WO | 2006/038031 | 4/2006 |
| WO | 2007/061787 | 5/2007 |
| WO | 2007/113494 | 10/2007 |
| WO | 2007/127802 | 11/2007 |
| WO | 2007/137211 | 11/2007 |

OTHER PUBLICATIONS

Lumsden AB, Chen C, et al. Nonporous silicone polymer coating of expanded polytetrafluoroethylene grafts reduces graft neointimal hyperplasia in dog and baboon models. Journal of Vascular Surgery 1996; v24 n5:825-833.

Sonoda H, Takamizawa K, et al. Coaxial double-tubular compliant arterial graft prosthesis: time-dependent morphogenesis and compliance changes after implantation. J Biomed Mater Res 2003; 65A: 170-181.

Sonoda H, Takamizawa K, et al. Small-diameter compliant arterial graft prosthesis: Design concept of coaxial double tublar graft and its fabrication. J Biomed Mater Res 2001; 55: 266-276.

◄─────► DIRECTION OF EXPANSION

◄─────► DIRECTION OF EXPANSION
◄───► DIRECTION OF COMPRESSION

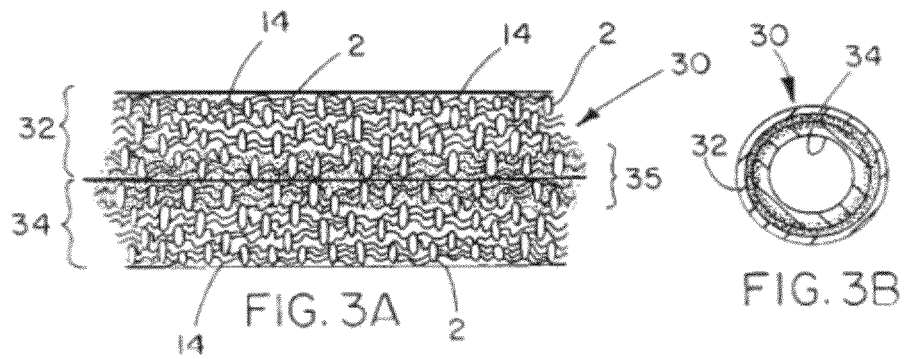
FIG. 3A
FIG. 3B
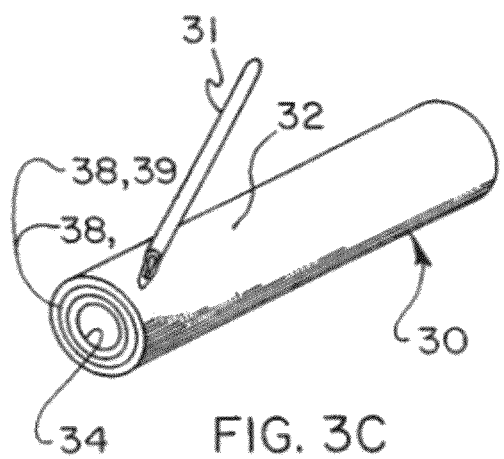
FIG. 3C
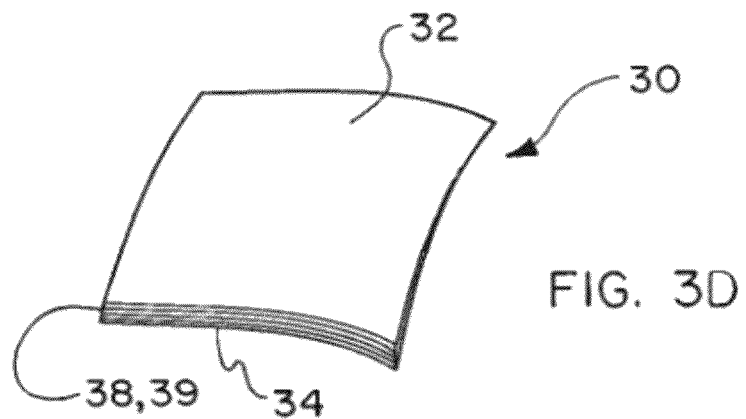
FIG. 3D

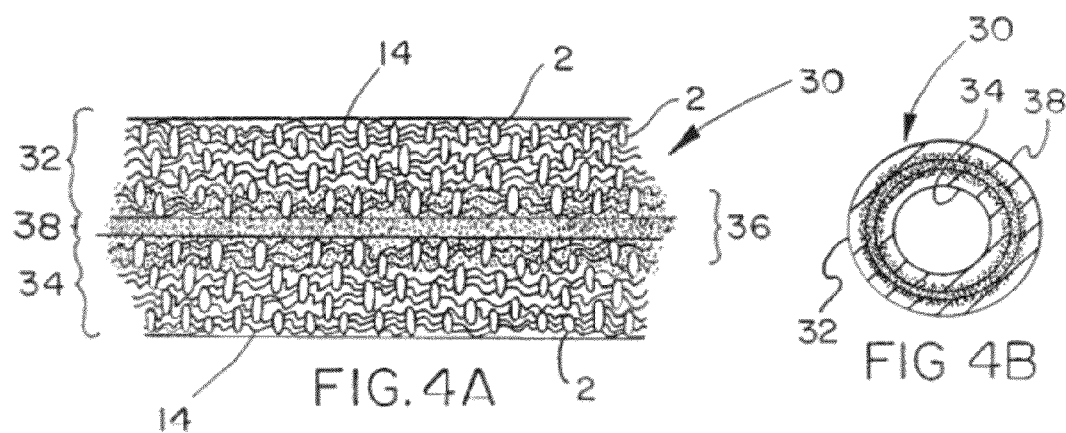
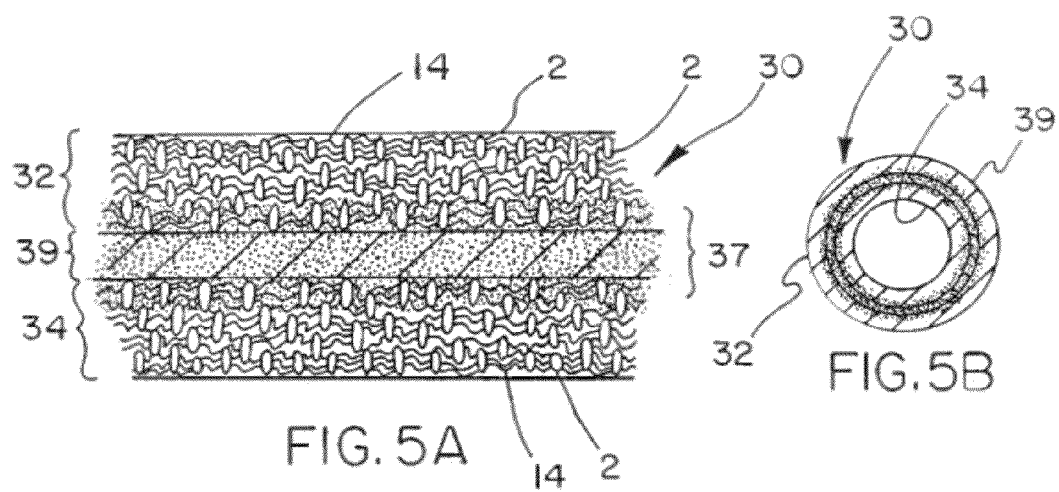

METHOD OF MAKING IMPLANTABLE DEVICES WITH REDUCED NEEDLE PUNCTURE SITE LEAKAGE

CROSS-REFERENCE TO RELATED APPLICATIONS

This application is a divisional application of application Ser. No. 10/999,276, filed Nov. 29, 2004 now U.S. Pat. No. 8,029,563.

FIELD OF THE INVENTION

The present invention relates to the field of implantable devices such as vascular grafts, patches and the like.

BACKGROUND OF THE INVENTION

A common problem with vascular grafts is bleeding through holes punctured through the wall of a graft by suture needles or dialysis needles. Commercially available vascular grafts are most conventionally made of polyethylene terephthalate fabric or porous polytetrafluoroethylene tubing but materials of biologic origin such as human or bovine arteries or veins have also been used. Suture needles used to create an anastomosis with these vascular grafts typically result in significant bleeding through the resulting holes that must be stopped prior to closure of the operative incision. Dialysis treatment of individuals suffering from renal failure requires that the blood of the individual be withdrawn, cycled through a dialysis machine and returned to the individual. A common approach to providing the necessary hemodialysis access is the use of an implanted arteriovenous vascular graft that may be subcutaneously cannulated by a dialysis needle connected to a dialysis machine via lengths of tubing. These dialysis needles may also produce undesirable bleeding at the puncture site upon their removal.

Vascular grafts presently used for hemodialysis access are typically implanted for about 14 days prior to cannulation with a dialysis needle so that the graft has had time to become surrounded by fibrotic tissue and thereby reduce the risk of hemorrhage about the outer surface of the graft following removal of the dialysis needle. A vascular graft for dialysis applications that allows early cannulation following implantation without compromising other positive characteristics would be a significant step forward in the field of hemodialysis access.

Suture line bleeding resulting from graft penetration by a suture needle is frequently aggravated by tension applied to the sutures during construction of the anastomosis, the tension generally resulting in elongation and enlargement of the hole created by the penetration of the suture needle. Bleeding through suture holes must be stemmed before the access incision can be closed. Suture hole bleeding is thus responsible for both increased blood loss and increased time of operation. A vascular graft offering reduced suture bleeding would be of value in both regards.

An arteriovenous access vascular graft is described by U.S. Pat. No. 4,619,641 to Schanzer, which teaches the construction of an access graft comprising two commercially available expanded polytetrafluoroethylene (ePTFE) tubular vascular grafts in coaxial relationship with a space of about 1 mm disposed between the inner and outer grafts. The space is filled with an elastomer such as silicone. While this construction may offer reduced bleeding after withdrawal of a dialysis needle, the graft is stiff and consequently difficult to work with during implantation. A similar construction is described by U.S. Pat. No. 6,719,783 to Lentz et al., expressly teaching that the inner and outer ePTFE grafts are of dissimilar porosity.

Della Coma et al., in U.S. Pat. No. 4,955,899, teach the manufacture of an ePTFE tubular graft having a coating of an elastomer. The graft is made by longitudinally compressing an ePTFE tube on a mandrel, and coating the compressed tube with the elastomer. After removal from the mandrel, the resulting graft has some degree of longitudinal compliance. However, providing an exposed outer surface of elastomer is generally deemed undesirable.

House et al., in U.S. Pat. No. 4,877,661, teach an ePTFE graft that offers longitudinal compliance without requiring an elastomer. This graft is made by placing an ePTFE tube on a mandrel and compressing it longitudinally, and subsequently exposing it to heat. The resulting ePTFE tube has bent fibrils (from the longitudinal compression and heat-setting) that act as hairpin springs, allowing for good bending properties with kink resistance and longitudinal compliance. While this graft is effective as a dialysis graft that bleeds less than a conventional ePTFE graft following the removal of a needle, even less bleeding would be desirable.

Sowinski et al., US 2004/0024442, teach an ePTFE tubular graft wherein an ePTFE tube is coated with an interpenetrating elastomer and compressed longitudinally. It is further taught that the coating and compression steps are interchangeable. A similar process and tube is taught by Tu et al., EP 0256748. U.S. Pat. No. 5,529,820 to Nomi et al. teaches an ePTFE tube provided with an interpenetrating coating of an elastomer on one surface, for use as an endoscope tube.

U.S. Pat. No. 5,061,276 to Tu et al. describes a vascular graft comprising a composite tube of ePTFE and an elastomer, having an outer layer of elastomeric polymer fibers wound under tension about the circumference of the graft to cause retraction of the tubing from its original size. The wrapping of elastomeric fibers is provided with the intention of making the graft more compliant.

Myers et al., U.S. Pat. No. 5,628,782, teach an ePTFE vascular graft for dialysis that provides a layer of fibers about the outer surface of an ePTFE tubular graft. The fibers are preferably provided with an outer covering of ePTFE film to retain the fibers to the graft surface. The presence of the fibers provides a large surface area to any blood escaping a puncture site, encouraging hemostasis. The fibers result in a somewhat bulky graft with poorer graft handling properties than many conventional vascular grafts. Another ePTFE vascular graft for dialysis is taught by Silverman et al. in U.S. Pat. No. 5,931,865. A multiple layer tubular construction is described, wherein one layer is under longitudinal compression relative to another layer.

Not withstanding the advantages of the above described devices, there remains a need for vascular grafts and other implantable devices that offer improved handling properties to the surgeon and further reduced leakage of body fluids such as blood following puncture by a suture needle or a dialysis needle.

SUMMARY OF THE INVENTION

The present invention relates to implantable devices such as prosthetic vascular grafts that, compared to conventional commercially available devices, offers a reduction in blood loss or other fluid loss when the device is punctured by a needle and the needle is subsequently removed. The device may be made to be relatively thin and flexible, and with longitudinal compliance (stretch), in order that it also offers good handling and kink resistance. While the device is preferably of tubular form, flat sheets or other forms may also be made.

The device has particular utility as a vascular graft, and more particularly as a vascular graft for kidney dialysis. It may also be useful for various other implantable device applications such as biliary or tracheal where a device that is resistant to fluid leakage following puncturing with a needle may be desired, such as to limit holes that may be formed in mounting a stent and graft together using a suture.

The device comprises at least inner and outer layers of a porous material having a microstructure of nodes interconnected by bent fibrils, and having void spaces between adjacent bent fibrils. The inner and outer layers are joined by an elastomeric adhesive that interpenetrates the void spaces of the adjacent surfaces of the inner and outer layers, that is, the inner surface of the outer layer and the outer surface of the inner layer. Optionally, a middle layer of an elastomeric material may also be provided, preferably joined to the inner and outer porous layers by the interpenetrating elastomeric adhesive. It has been found that good adhesion is obtained between layers with only a small depth of interpenetration into the wall of the porous material.

Preferably, the inner and outer layers of porous material having a microstructure of nodes interconnected by bent fibrils is expanded polytetrafluoroethylene (ePTFE). This material has a long history of use in various implant applications, including blood contact applications such as sutures, vascular grafts and stent-grafts. It is believed that other biocompatible materials with node-and-fibril microstructures may also be used, such as polypropylene or ultra-high molecular weight polyethylene. The elastomeric material may be a material such as silicone rubbers, polyurethanes or fluoroelastomers (such as, for example, taught by published patent application WO 2004/012783). It is not required that the elastomeric material be a cross-linked material. The elastomeric material may optionally be porous. For the present invention, "elastomeric materials" are considered to be polymeric materials capable of being stretched in one direction at least ten percent by the application of a relatively low force and, upon release of the force, will rapidly return to approximately the original dimension (i.e., the dimension that the material had prior to the application of the stretching force).

Further, as an alternative to, or in addition to, the elastomeric material as a middle layer, the graft may incorporate an additional component (e.g., metal or plastic) in the construction in a way that provides stretch and reduced needle puncture site leakage behavior to the construction. This can be accomplished by, for example, a superelastic metal such as a nitinol wire formed into a stent, such as tubular braided structure or a metallic wire formed into a ring or helical structure. This offers good flexibility for bending, transverse compression resistance and provides longitudinal "stretch" into the construction.

While the preferred embodiment of the graft is made with two layers of graft material and an intermediate elastomeric layer, the graft may also have additional layers. For example, three layers of graft material may be used alternating with two layers of elastomeric material. For all embodiments, the graft layers may all be of the same material or the graft layers may be different in one or more characteristics (e.g., wall thickness or mean fibril length). Likewise, if more than a single elastomeric layer is used, the layers may be the same or may have different characteristics. It is also apparent that a graft may be made with different constructions along different portions of its length.

The graft of the present invention has longitudinal stretch. The length of the graft may be extended by applying a slight amount of tension to the graft (e.g., by hand). After the tension is released, the graft will quickly recover to about the original length prior to the application of tension.

Tubular grafts may have a constant diameter between graft ends, or alternatively may be tapered, whereby one end of a tubular graft has a smaller diameter than the opposing end. Other configurations may also be appropriate, including bifurcated devices and stepped wall configurations.

The combination of inner and outer porous tubes with bent fibrils and the middle layer of elastomeric material offers the highly desirable and heretofore unachieved combination of reduced leakage following removal of a needle from a puncture site, along with good biocompatibility, longitudinal stretch and good handling and bending properties. The good bending properties appear to be the result of the use of inner and outer porous tubes having bent fibrils, on either side of the elastomeric material. The bent fibrils adjacent the outer meridian of a bent tube are able to extend (unbend or straighten) while the fibrils adjacent the inner meridian of the bent tube are able to bend still further, thereby enabling the tube to bend smoothly without kinking. It also offers good suture retention, along with reduced suture line bleeding. Because of the reduced bleeding from needle penetration, a vascular graft made in accordance with the present invention, when used for dialysis applications, may allow early cannulation during the period of time following implantation that is normally reserved for healing prior to initial cannulation.

BRIEF DESCRIPTION OF THE DRAWINGS

FIG. 3A describes a schematic longitudinal cross sectional view of the wall of a device of the present invention having two layers of porous material having bent fibrils, wherein the two layers are joined by an elastomeric adhesive.

FIG. 3B describes a transverse cross sectional view of a tubular device made according to FIG. 3A.

FIG. 3C is a perspective view of a tubular device shown with a dialysis needle.

FIG. 3D is a perspective view of a sheet graft.

FIG. 4A describes a schematic longitudinal cross sectional view of the wall of a device of the present invention having two layers of porous material having bent fibrils, wherein the two layers are joined by an elastomeric adhesive and wherein the elastomeric adhesive separates the two layers of porous material.

FIG. 4B describes a transverse cross sectional view of a tubular device made according to FIG. 4A.

FIG. 5A describes a schematic longitudinal cross sectional view of the wall of a device of the present invention having two layers of porous material having bent fibrils, wherein the two layers are separated by a layer of an elastomeric material and wherein all layers are joined by elastomeric adhesive.

FIG. 5B describes a transverse cross sectional view of a tubular device made according to FIG. 5A.

DETAILED DESCRIPTION OF THE DRAWINGS

Figure 1:
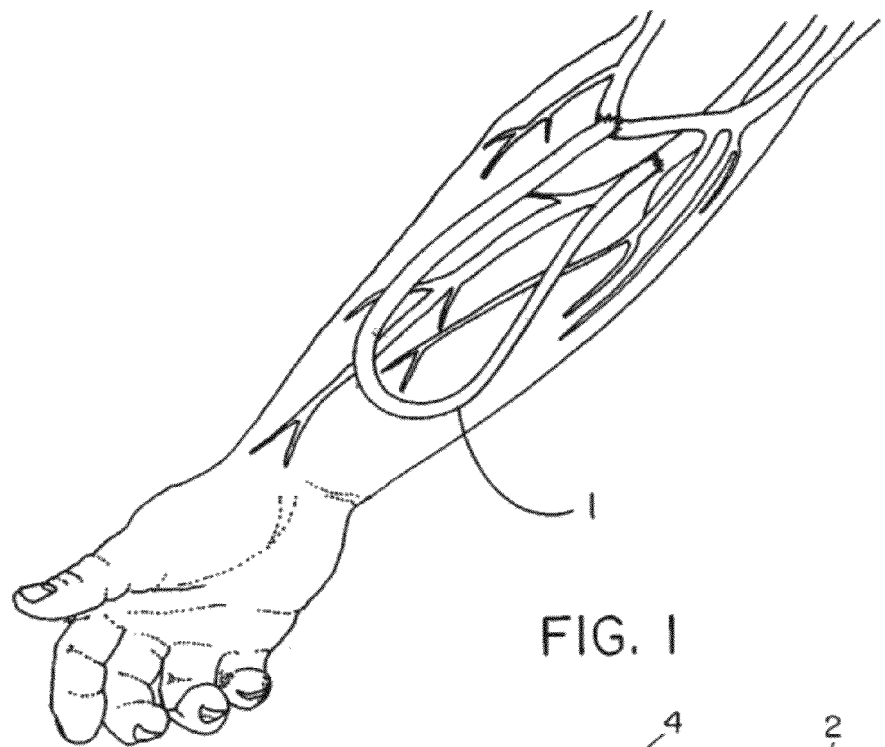
FIG. 1 is a view of a typical vascular graft after implantation in a human forearm for use as a dialysis graft.

FIG. 1 is a view of a typical vascular graft after implantation in a human forearm for use as a dialysis graft 1. The relatively small radius bend of graft 1 at its distal end is apparent.

Figure 2A:
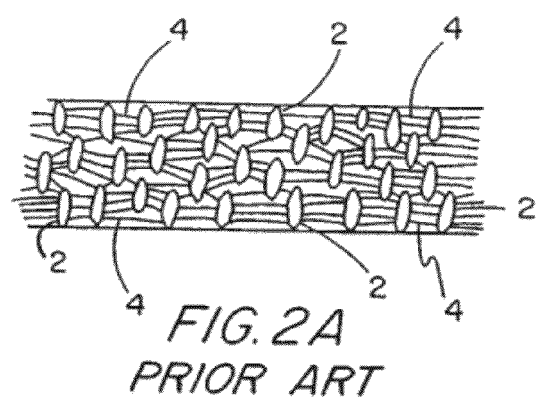
FIG. 2A describes a schematic representation of a node and fibril microstructure of the prior art wherein the fibrils are relatively straight.

FIG. 2A is a schematic representation of a cross section of a porous material having a microstructure of nodes 2 interconnected by fine fibrils 4, with void spaces between adjacent fibrils. This microstructure as shown is generally typical of ePTFE. The interconnecting fibrils are relatively straight (the straightness is exaggerated in FIG. 2A). FIG. 2B is a scanning electron photomicrograph (500× magnification) of a node and fibril microstructure of the prior art wherein the fibrils are relatively straight.

Figure 2C:
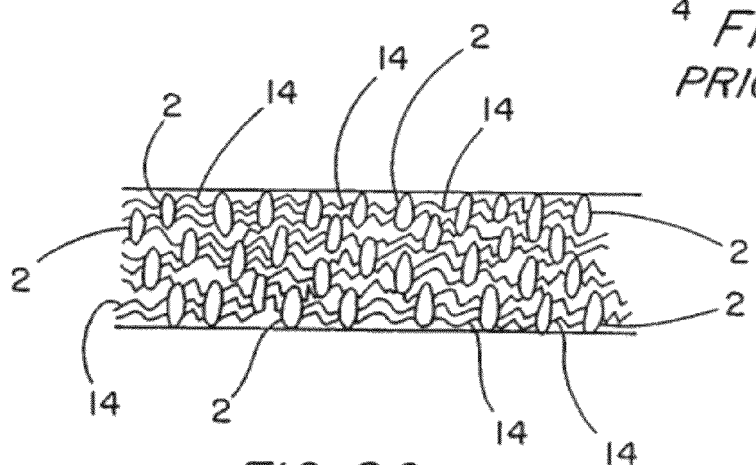
FIG. 2C describes a schematic representation of a node and fibril microstructure of the prior art wherein the fibrils are bent.
Figure 2B:
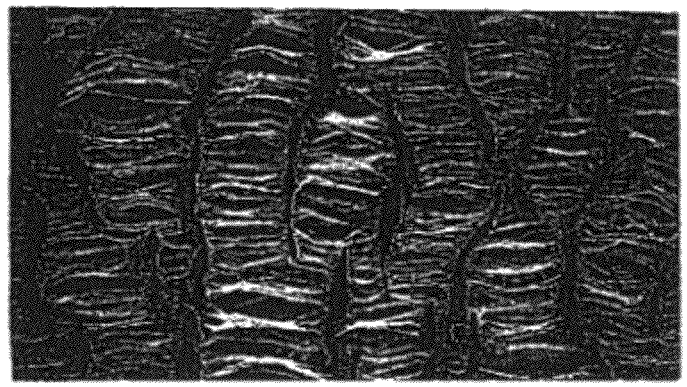
FIG. 2B is a scanning electron photomicrograph (500× magnification) of a node and fibril microstructure of the prior art wherein the fibrils are relatively straight.
Figure 2D:
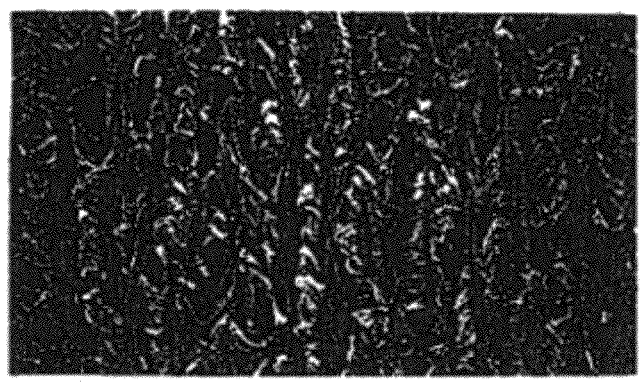
FIG. 2D is a scanning electron photomicrograph (500× magnification) of a node and fibril microstructure of the prior art wherein the fibrils are bent.

FIG. 2C describes a schematic representation of a cross section of a porous material having a microstructure of nodes 2 interconnected by fine bent fibrils 14, again with void spaces between adjacent fibrils. FIG. 2D is a scanning electron photomicrograph (500× magnification) of a node and fibril microstructure of the prior art wherein the fibrils are bent. These materials are generally made by using materials as shown in FIGS. 2A and 2B as precursors. The precursor materials are compressed lengthwise (e.g., to about half of the length of the precursor) to cause the fibrils to bend, and then heat-treated (e.g., for 3 minutes in an oven set at 380° C.). Tubular precursors are longitudinally compressed by placing them onto a mandrel (preferably of stainless steel, Inconel®, or other heat-resistant material) over which they are a snug fit prior to subjecting the tube to longitudinal compression and heat treating; the mandrel is removed after being allowed to cool. These materials exhibit longitudinal stretch resulting from the bent fibrils 14. Tubes made by this method have good bending and handling properties and good kink resistance. For longitudinally extruded and expanded tubular forms, FIGS. 2C and 2D would typically describe longitudinal cross sectional views.

Mean fibril lengths of these materials can be varied by known manufacturing methods, and may range, for example, from a few microns or less, to one hundred microns or more. The mean fibril length is determined from a photomicrograph of preferably a longitudinal cross section of the sample wall, or alternatively, of a representative surface of the sample. The mean fibril length is considered to be the average of ten measurements, made in the predominant direction of the fibrils of the distance between nodes connected by fibrils. The ten measurements are made by first verifying that the photomicrograph of a representative region of the sample is of adequate magnification to show at least five sequential fibrils within the length of the photomicrograph. A series of five measurements are taken along a straight line drawn across the surface of the photomicrograph in the predominant direction of the fibrils followed by a second series of five measurements made along a second line drawn parallel to the first. Each measurement constitutes the distance between adjacent nodes connected by at least one fibril. The ten measurements obtained by this method are averaged to obtain the mean fibril length of the region.

Samples having bent fibrils should be moderately tensioned as necessary to substantially straighten the fibrils prior to mean fibril length determination. For very thin ePTFE materials such as thin films, mean fibril lengths may be estimated by visual examination of scanning electron photomicrographs of adequate magnification to show numerous full-length fibrils within the boundary of the photomicrograph.

The bent character of the fibrils can also be quantified, also using a photomicrograph as described above that is of adequate magnification to show at least five sequential fibrils along the length of the photomicrograph. The material sample must be in its relaxed state (i.e., under no tension or compression) when photographed; it should be allowed to relax for 24 hours in the relaxed state at room temperature prior to being photographed. The photomicrograph is marked with two parallel drawn lines spaced 24 mm apart, approximately centered on the photograph and oriented so that the lines are substantially parallel to the direction of the fibrils. Moving from left to right along the top drawn line, internodal distance "H" is determined to be the distance between the node attachment points of the first distinct fibril closest to the drawn line. A distinct fibril is one whose complete length can be visually distinguished. Vertical displacement, a distance "V", is next measured as the perpendicular length from distance "H" to the farthest point on the fibril. If the fibril crossed distance "H" one or more times, then distance "V" is determined to be the sum of the maximum perpendicular "V" measurements. The ratio of V/H is calculated for the fibril. Moving to the right along the drawn line, "V" and "H" measurements are determined for four additional fibrils. The photograph is rotated 180 degrees and the process is repeated for five additional fibrils. Mean values of "V", "H", and V/H are calculated for all ten fibrils examined. Samples with bent fibrils will typically have a V/H ratio of greater than about 0.15.

FIG. 3A describes a schematic representation of a cross section of the present invention 30. Two ePTFE layers 32 and 34, both having bent fibrils 14, are joined by an elastomeric coating shown as dot-shaded region 35 extending into the void space of a portion of the thickness of both layers adjacent to the contacting surfaces of the two ePTFE layers 32 and 34. For the preferred tubular form (shown in transverse cross section by FIG. 3B), FIG. 3A can be considered to schematically represent a longitudinal cross sectional view wherein layer 32 is an outer layer and layer 34 is an inner layer. FIG. 3C illustrates a perspective view of a tubular embodiment (showing optional middle layers 38 or 39, subsequently described in detail), as it would appear about to be cannulated by a typical dialysis needle 31. Planar or sheet embodiments of the graft 30, such as shown by the perspective view of FIG. 3D, may be made by simply cutting finished tubes longitudinally, or by being fabricated in sheet form initially. Such sheets are relatively flexible and can be curved appropriately to conform to the shapes of various body components.

A preferred method of making the tubular embodiment begins with fitting an ePTFE precursor tube over a mandrel (preferably stainless steel or nickel-chromium-iron alloy such as Inconel®) with a slight interference fit between the outer diameter of the mandrel and the inner diameter of the ePTFE tube. The tube is fitted without longitudinal compression, that is, in a longitudinally extended state with the fibrils in their substantially straight conventional condition (according to FIG. 1). While ePTFE precursor tubes having bent fibrils may be used, they are not required. A relatively thin coating of a desired elastomeric material is then applied to the outer surface of the ePTFE tube fitted over the mandrel. A preferred elastomeric material is MED-1137 Adhesive Silicone Type A from NuSil Silicone Technology (Carpenteria, Calif.). The application of the elastomeric adhesive may be accomplished by various means such as spraying, dip coating, brushing or by spreading with gloved fingers. After the outer surface of the inner ePTFE tube has been coated with the elastomeric adhesive, a second ePTFE tube is fitted over the first, preferably with a small amount of interference between the inside diameter of the outer ePTFE tube and the outer diameter of the inner tube. The pair of coaxially-fitted ePTFE tubes are then longitudinally compressed while still fitted over the mandrel. The amount of longitudinal compression is a function of the desired amount of longitudinal stretch in the completed graft; more longitudinal compression provides a greater amount of longitudinal stretch. A desirable amount of longitudinal compression may be, for example, about 100 percent (i.e., the coaxial tubes are compressed to half of their original length). The amount of longitudinal compression may thus be 10%, 20%, 30%, 40%, 50%, 60%, 70%, 80%, 90%, 100%, 110%, 120%, 130%, 140%, 150%, 160%, 170%, 180%, 190%, 200%, etc. (i.e., until wrinkling and significant non-uniform deformation of the tube occurs).

Following longitudinal compression, the adhesive is cured. It may be allowed to cure at ambient temperature or may be cured by other means such as the use of heat above ambient.

Following curing, the coaxial tubes 32 and 34 are removed from the mandrel. The adhesive will have interpenetrated the fitted surfaces of the tubes to some portion of the thickness of each tube. This results in good mechanical adhesion of the coaxial tubes. The presence of the cured elastomeric material holds the coaxial tubes 32 and 34 in a state of longitudinal compression whereby the length of the resulting coaxial graft 30 is less than that of the longitudinally extended length of the precursor tubes as fitted over the mandrel prior to the longitudinal compression step. Both the inner tube 34 and outer tube 32 have bent fibrils 14 resulting from the cured elastomeric material holding the coaxial tubes in a longitudinally compressed state.

The bent fibrils 14 provide the resulting graft 30 with good handling and bending properties, as well as kink resistance. The combination of the bent fibrils 14 of the two ePTFE layers 32 and 34 and the presence of the silicone adhesive at the joined surfaces of the two ePTFE tubes (region 35 of FIG. 3A) provides reduced bleeding at a needle puncture site during use.

The chosen tubes may have fibril lengths as desired; it is not required that both tubes have equivalent fibril lengths. Tubes having different fibril lengths at their inner and out surfaces are known and may be used for either or both tubes.

The selected tubes may have annular or helically-oriented densified segments alternating with un-densified segments along their length for additional hoop strength if desired. A preferred process for making such a radially supported ePTFE tubular structure is sequentially described as follows. A longitudinally extruded and expanded ePTFE tube is obtained and fitted coaxially over a mandrel having an outside diameter the same as or slightly larger than the inside diameter of the ePTFE tube. The ends of the tube are then pushed together so that the length of the tube is at least about 50%, and preferably about 20%, of the original length of the tube prior to this longitudinal compression. The tube and mandrel are then heated in an air convection oven set at 380° C. for approximately 50 seconds. Next, predetermined regions of the compressed tube are heat-treated via the use of a laser (e.g., a model 2010, 20W $CO_2$ laser with a 6.35 mm focal length lens, Applied Laser Technology, Inc., Scottsdale, Ariz.) directed toward the rotating surface of the tube where a densified region is desired. Subsequent to the laser treatment and cooling, the graft is removed from the mandrel. With moderate tension applied to the ends of the graft, the portions not treated by the laser readily extend out to their original length. The portions treated by the laser, however, are not readily extendible. These denser portions provide the radial support to the graft.

Optionally, either or both tubes may have a helical wrap of ePTFE film for increased hoop strength. The outer surface of the coaxial graft may also be provided with a reinforcing structure such as rings or a helical structure of a material such as non-porous PTFE or fluorinated ethylene propylene (FEP). The reinforcing rings (or the reinforcing helical structure) may optionally be provided so as to be removable during surgery. The reinforcing material may be metal, such as nitinol wire (e.g., as a braided structure with fine wire) or stainless steel, or may be plastic or other suitable material. It is apparent that a reinforcing structure may be provided within the coaxial structure, between the joined surfaces of the inner and outer tubes.

It is also apparent that the tubular structure may be used as the graft component of a stent graft when fitted to a stent component. The stent may be exterior to the graft, or the graft may be exterior to the stent. Likewise, the stent component may be provided between the two coaxial tubes, in the region of the interface.

The graft may be provided with a variety of therapeutic agents for a variety of purposes, such as anti-inflammatory, anti-bacterial or anti-thrombogenic drugs. Such agents and treatments are known in the vascular graft and stent fields.

The chosen tubes may have wall thicknesses as desired. Their wall thicknesses may be the same or they may be chosen to be different. Generally, it is preferred that the combined wall thicknesses be relatively thin for good handling, for example, about 0.8 mm or less in combined thickness (e.g., a wall thickness of about 0.7 mm, 0.6 mm, 0.5 mm, 0.4 mm, 0.3 mm, 0.2 mm or 0.1 mm). It is apparent that a greater wall thickness generally improves the reduction in puncture site bleeding, but at the expense of the surgical handling properties of the graft. Therefore, the chosen total wall thickness may be something of a compromise between those characteristics.

The amount of interpenetration of the elastomeric adhesive into the joined surfaces of the coaxially-fitted porous tubes is a function of variables including the amount of elastomeric material applied, the method of application, the type of elastomeric material chosen, curing technique and the viscosity of the elastomeric material. It is apparent that these variables will also affect the graft handling and the amount of reduction in puncture site leakage that will be achieved. It is likewise apparent that the degree of interpenetration may be kept minimal in order that only a small percentage of the thickness of each of the inner and outer tubes is affected. Alternatively, the adhesive may interpenetrate to the outer and/or inner surfaces of the coaxial graft. The adhesive may be provided so as to maintain the porous character of the graft through its thickness (i.e., between the inner and outer surfaces). Alternatively, the adhesive may be applied to render the coaxial graft impervious through its thickness, precluding the passage of body fluids or other biologic components through the thickness of the graft.

As shown by the schematic longitudinal cross section of FIG. 4A and the transverse cross section of the tubular embodiment of FIG. 4B, the adhesive may be applied in an amount that results in a layer 38 of adhesive between inner layer 34 and outer layer 32, so that the inner surface of outer layer 32 is separated from and not in contact with the outer surface of inner layer 34. The adhesive may still interpenetrate into the void spaces of both layers 32 and 34 beyond these surfaces, as indicated by dot-shaded adhesive-coated region 36.

FIG. 5A describes a schematic representation of a cross section of an alternative embodiment wherein graft 30 includes a discrete layer 39 of elastomeric material. The preferred embodiment is again tubular (shown by the transverse cross section of FIG. 5B), for which FIG. 5A would represent a longitudinal cross section of the wall of such a tubular graft 30. Discrete layer 39 of elastomeric material is preferably adhesively joined to the inner surface of outer tube 32 and the outer surface of inner tube 34 by an elastomeric adhesive.

The tubular embodiment of FIGS. 5A and 5B is made by fitting a selected ePTFE tube over a mandrel with a slight interference fit. The ePTFE tube is fitted in its extended state (without longitudinal compression) so that the fibrils are in a substantially straight condition. The outer surface of the ePTFE tube is coated with elastomeric adhesive as described above. A length of elastomeric tubing (e.g., silicone tubing) is obtained having an inside diameter of about equal dimension to the outside diameter of the ePTFE tube fitted over the mandrel. The length of elastomeric tubing should be greater than the length of the mandrel. The length of elastomeric tubing is carefully fitted over the adhesive-coated outer surface of the ePTFE tube. The ends of the elastomeric tubing should extend beyond the ends of the mandrel. An overhand knot is tied in one end of the elastomeric tubing that extends beyond the end of the mandrel. Tension is applied to the length of elastomeric tubing from the end opposite the knot. The tension is maintained by securing the tensioned end to the same end of the mandrel by suitable means. For example, while maintaining tension so that the elastomeric tubing is in a longitudinally-stretched state, another overhand knot is tied in the opposite end of the elastomeric tubing that extends beyond the end of the mandrel opposite the first knot, thereby maintaining the tension on the elastomeric tubing by the pair of knots securing the elastomeric tubing beyond the ends of the mandrel.

The outer surface of the tensioned elastomeric tubing is then coated with elastomeric adhesive, after which a second ePTFE tube is fitted under a small amount of tension over the tensioned elastomeric tubing. Both coatings of the elastomeric adhesive are then cured (or allowed to cure) while the intermediate layer of elastomeric tubing remains in tension. After curing is complete, one of the knots in the elastomeric tubing may be untied from one end of the mandrel or alternatively may be transversely cut free of the remainder of the coaxial construct, allowing the construct to be removed from the opposite end of the mandrel. Following removal, both ends of the construct may be cut transversely to dispose of the second knot and provide a graft with squarely-cut clean ends.

When the first knot in the elastomeric tubing is removed by untying or cutting, the tension in the length of the elastomeric tubing is released and the elastomeric tubing will recover most or all of its original, shorter pre-tension length. This recovery applies compression to the inner 34 and outer 32 ePTFE tubes, causing the fibrils of the ePTFE tubes 32 and 34 to become bent fibrils 14.

It is apparent that the amount of longitudinal stretch available in the completed graft 30 will be a function of the amount of tension or stretch applied to the elastomeric tube during the construction process. This amount may be described as a function of the length change between the transversely cut ends of the graft as measured prior to cutting and releasing the tension on the stretched elastomeric tube, and measured again after cutting and removal of the completed graft from the mandrel.

The bent fibrils 14 of the resulting graft 30 also provide this embodiment with good handling and bending properties, as well as kink resistance. The combination of the bent fibrils 14 of the two ePTFE layers 32 and 34 and the presence of the elastomeric adhesive at the joined surfaces of the two ePTFE tubes and the discrete layer 39 of the elastomeric tubing provides reduced bleeding at a needle puncture site during use.

Figure 5C:
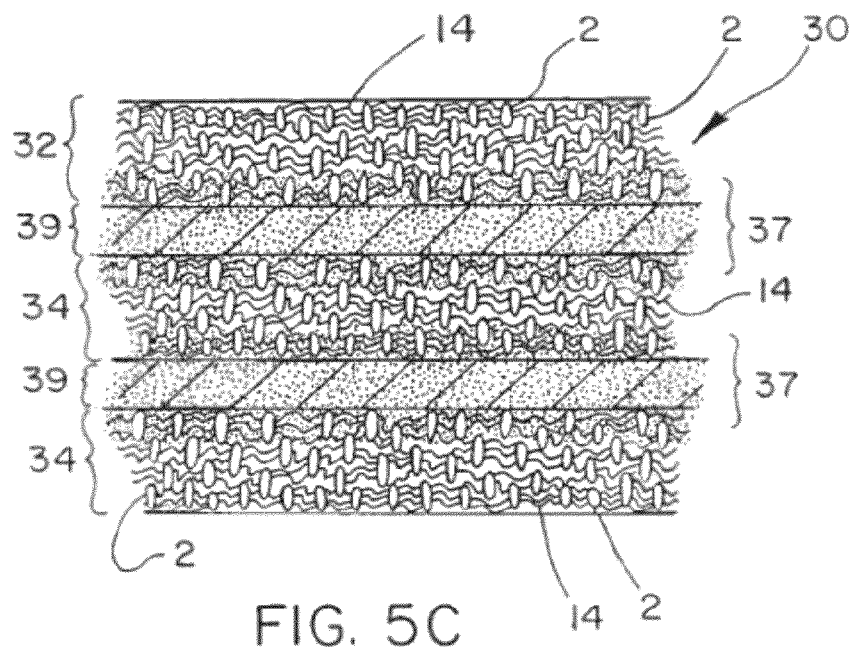
FIG. 5C is a schematic longitudinal cross sectional view of the wall of a device made as shown in FIG. 5A, differing only in having additional layers of porous material and elastomeric material.

While the preferred embodiment of the graft is made with two layers of graft material and an intermediate elastomeric layer, the graft may also have additional layers. For example, three layers of graft material may be used alternating with two layers of elastomeric material. FIG. 5C is a schematic longitudinal cross sectional view of the wall of a graft made as shown in FIG. 5A, differing only in having additional layers of porous material and elastomeric material. It is apparent that various combinations of multiple layers may be created as desired for any of the various embodiments.

For all embodiments, the graft layers may all be of the same material or the graft layers may be different in one or more characteristics (e.g., wall thickness or mean fibril length). Likewise, if more than a single elastomeric layer is used, the layers may be the same or may have different characteristics.

Figures 6A, 6B:
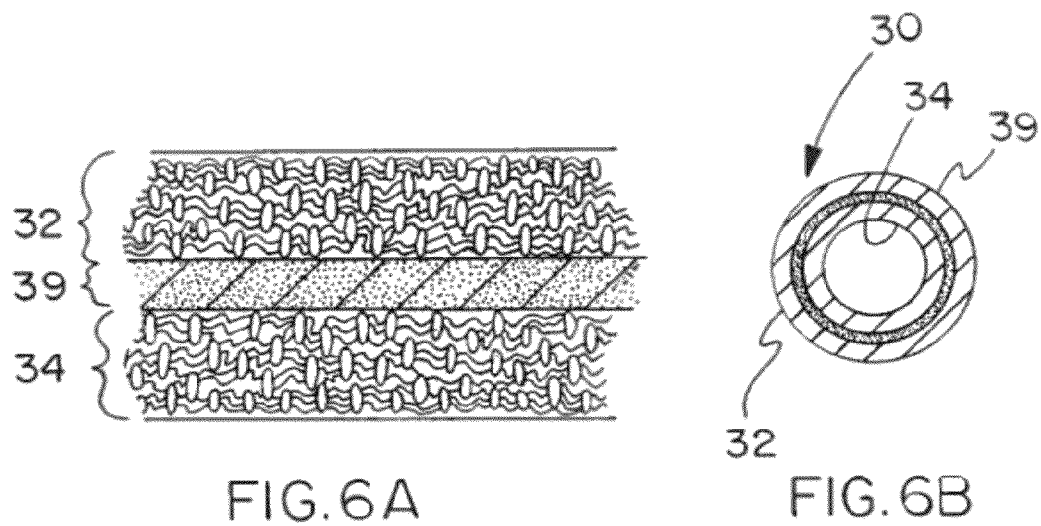
FIGS. 6A and 6B are analogous to FIGS. 5A and 5B respectively, with the difference that there is little or no interpenetrating elastomeric adhesive; the tubes fit together by diametrical interference, or by the use of a non-interpenetrating adhesive, or by thermal bonding.

FIGS. 6A and 6B describes a schematic cross sectional representation of an alternative to that of FIG. 4A wherein no interpenetrating elastomeric adhesive is used and the ePTFE tubes are simply an interference fit with the elastomeric tubular layer 39. Likewise, an adhesive may be used in place of the interference fit wherein the adhesive is applied as a discontinuous pattern such as a dot matrix, and thus only interpenetrates the area that it contacts the ePTFE tube surfaces. Such a discontinuous adhesive would not be required to be an elastomeric adhesive.

Various examples of the present invention were manufactured using tubular graft materials of different types (e.g., wall thickness) and with different elastomeric materials for the intermediate layer. Following manufacture (including curing of the elastomeric materials), the completed grafts were subjected to a cannulation test wherein the graft was subjected to water pressure and cannulated with a needle. The results of such a test are considered as comparative indicators only, due to the entirely different behavior of such cannulated grafts when implanted and containing flowing blood under pressure.

Testing generally consisted of pressurizing each example individually with water at 150 mm Hg at room temperature, cannulating the sample device with a 15 gauge dialysis needle, removing the needle and applying digital pressure to the needle hole for a short period, typically about 10 seconds. After removal of the digital pressure, the flow rate (ml/minute) of water escaping from the needle hole was measured using a positive displacement flow sensor (Cole-Parmer Instruments Model No. MA0-125-T-20-AA connected to a digital display). Due to the non-linearity of the flow meter, the calibrated system is used with appropriate correction factors applied as required.

A vertical water column was used to supply the pressure for this leak testing of each example. Each example was tested in a horizontal position and at the same elevation with respect to the water column. The example graft to be tested was connected to the base of the water column by a short length of tubing having a barbed fitting at the end of the tubing to which the graft was fitted by interference. The opposite end of the example graft was clamped closed using a forceps. Each tested example was checked to ensure that it did not leak any water prior to cannulation. A randomly selected location between the graft ends was cannulated with a new 15 gauge stainless steel needle (Monoject 200 aluminum hub hypodermic 15×1.5 inch B bevel, Sherwood Medical, St. Louis, Mo.). The needle was then removed and digital pressure was applied to the location of the needle hole for about ten seconds and released for 40 seconds. This use of digital pressure was intended to simulate any effect resulting from the conventional use of digital pressure on dialysis patients. Digital pressure was again applied for about one second, released for one second, applied again for one second and released. Seventy seconds after final release of digital pressure, the indicated flow rate was recorded.

Cannulation was accomplished by inserting the point of the needle into an upper surface of the graft with the bevel of the needle facing upwards, that is, away from the surface of the graft. The point of the needle was inserted through the graft so as to intersect the longitudinal axis of the graft. The needle was always aligned with the graft so that the longitudinal axis of the needle and the longitudinal axis of the vascular graft lay in a common plane during cannulation. Each needle was oriented at an angle of about 45 degrees with respect to the longitudinal axis of the graft. Care was taken not to damage the opposite or lower surface of any tested example during cannulation of the upper surface.

Conventional 6 mm inside diameter ePTFE vascular grafts will show a leak flow rate of typically greater than about 200 ml/minute when cannulated on this test fixture by the described method.

EXAMPLE 1

An example was made generally according to FIGS. 5A and 5B. Two 15 cm lengths of 6 mm inside diameter ePTFE tubing, made by longitudinal extrusion and expansion (i.e., with fibrils that are substantially parallel to each other and oriented in a direction parallel to the length of the tubing), were cut from a longer length. This tubing had a wall thickness of about 0.4 mm and a mean fibril length of about 22 microns.

One of the 15 cm lengths of ePTFE tubing was fitted over a stainless steel mandrel that provided a slight interference fit. Tension was applied to the ends of the ePTFE tube by hand to assure that the tube was not under any longitudinal compression and that the fibrils of the microstructure were substantially straight. This tensioning step was not deemed to be critical but helped ensure uniformity of the resulting graft.

Both ends of the ePTFE tube were temporarily secured to the mandrel by helically wrapping a strip of thin ePTFE film around each end of the tube. A coating of medical grade silicone adhesive (Adhesive Silicone Type A, Med-1137, NuSil Silicone Technology, Carpenteria Calif., diluted 20% by volume with heptane) was applied to the outer surface of the ePTFE tube using gloved human fingers.

A 30 cm length of silicone tubing was obtained (Part No. T050PLAT374X354, Jamak Corp., Weatherford, Tex.). This tubing had an inside diameter of about 9.0 mm and an outside diameter of about 9.5 mm. This length of silicone tubing was carefully fitted over the adhesive-coated outer surface of the ePTFE tube. An overhand knot was tied in one end of the silicone tube that protruded beyond the end of the mandrel. Tension was applied to the opposite end of the silicone tube that protruded beyond the opposite end of the mandrel, causing the silicone tubing to neck down with regard to its inside diameter and come into full contact with the underlying adhesive-coated surface of the ePTFE tube. This opposite end of the tensioned silicone tube was then temporarily secured to the outer surface of the mandrel (extending beyond the end of the ePTFE tube) by a tightly-wound wrapping of a strip of thin ePTFE film, applied by hand. A coating of the same silicone adhesive was then applied to the outer surface of the tensioned silicone tubing.

The second 15 cm length of ePTFE tubing was forced onto the outer surface of an 8 mm diameter stainless steel mandrel, thereby distending the 6 mm inside diameter ePTFE tube diametrically. The diametrically distended 15 mm length of ePTFE tube was then carefully fitted over the adhesive-coated, tensioned silicone tubing working from the end secured to the mandrel by the ePTFE film wrapping. When coaxial with the inner ePTFE tube, slight tension was applied to the ends of the outer ePTFE tube to assure that there was no longitudinal compression on the ePTFE tube and that the fibrils of the microstructure were substantially straight. Finally, an outer helical wrap of ePTFE film was applied temporarily to the outer surface of the outer ePTFE tube to ensure good contact between the three underlying layers.

The entire construction process was completed relatively quickly, before any significant curing of the silicone adhesive layers was effected. On completion of this construction, it was set aside overnight, in a room temperature environment, to allow the two layers of silicone adhesive to cure.

After adhesive curing, the outer helical wrap of ePTFE was removed. Both ends of the resulting graft were trimmed by cutting transversely through all three layers adjacent the ends of the ePTFE tubes with a sharp blade, after which the graft was removed from the mandrel. The length of the resulting graft was about 55% of the original length of the ePTFE tubes due to axial compression applied to those tubes by the releasing of the previously-applied axial tension on the silicone tubing. The resulting graft had a wall thickness of about 1.0 mm as measured by the opposing flat faces of the jaws of calibrated digital calipers (used for all example wall thickness measurements described herein). When subjected to the dialysis needle cannulation test, the graft demonstrated a leakage of about 16 ml/minute. The graft showed good bending properties and offered longitudinal stretch.

EXAMPLE 2

Another example was created in the same manner as described for Example 1 except that both ePTFE tubes were tubes of greater wall thickness and had been processed by being longitudinally compressed and heat-treated to provide them with bent fibrils prior to construction of the example. These precursor tubes had a wall thickness of about 0.6 mm.

The resulting graft had a wall thickness of about 1.0 mm. It appeared that the wall thickness was the result of the relatively tight overwrap of the temporarily applied helical film wrap used during construction. When subjected to the dialysis needle cannulation test, the graft demonstrated a leakage of about 19 ml/minute. The graft showed good bending properties and offered longitudinal stretch.

EXAMPLE 3

An example of a tubular graft generally according to FIGS. 3A and 3B was made using the same ePTFE tubing as used for Example 1. A length of this ePTFE tubing was fitted over a mandrel and secured as described for Example 1, and coated with the same silicone adhesive in the same manner. The second tube was, also as described for Example 1, distended to an inside diameter of 8 mm. The second ePTFE tube was then coaxially fitted over the first, adhesive-coated ePTFE tube, with tension applied to the ends of the second tube to assure that it was fully extended longitudinally (with the fibrils of the microstructure in a substantially straight condition). A temporary helical wrap of a strip of thin ePTFE film was uniformly applied about the outer surface of the outer tube. The coaxial tubes were then longitudinally compressed together, by applying a compressive force to both tubes by pushing the opposing ends of the tubes toward each other by hand. No wrinkling or gross deformation of the tubes resulted, in part due to the temporary helical wrap of ePTFE film. The compressed length of the coaxial tubes was slightly less than half of the length prior to longitudinal compression. The resulting assembly was set aside overnight at room temperature to allow the silicone adhesive to cure.

Following overnight curing, the temporary ePTFE helical film wrap was removed. The ends of the graft were trimmed by cutting transversely with a sharp blade, after which the graft was removed from the mandrel.

The resulting graft had a wall thickness of about 0.9 mm. When subjected to the dialysis needle cannulation test, the graft demonstrated a leakage of about 50 ml/minute. The graft showed reasonably good bending properties, and offered longitudinal stretch.

When two samples made according to this description were stretched using an Instron® tensile tester at a rate of 100 mm/min, the samples stretched an average of about 12.5% under a 0.25 kg force, about 36.5% under a 0.5 kg force, and about 54% under a 1 kg force (Instron® Model No. 5564 (Canton, Mass.) fitted with a 10N load cell and Part No. 2712-002 pneumatically-operated grips (pressure supplied at 276 KPa) with Part No. 2702-003 knurled 25 mm by 12 mm faces, with the long axis of the face oriented to be parallel to the test axis). Both grafts quickly recovered to about their original length on the release of the length extending force.

Two additional samples were made according to this description, with one of the two samples longitudinally compressed as described for this example and the other not compressed. The result was that the first of these two grafts had bent fibrils and the second did not. Their bending behavior was compared by gently and progressively bending each sample in comparison to plastic templates with semi-circular cut-outs of different radii, in increments of 1.6 mm (1/16 inch), noting the radius at which each sample kinked. Each of these gauges thus defined the outside radius of the bend, that is, the radius of the outer meridian of the bent tube. The tubular sample with the bent fibrils kinked at a bend radius of about 14.3 mm, while the sample with the straight fibrils kinked at a bend radius of about 31.8 mm. The tubular sample of the present invention could thus be bent at radii of 30 mm, 25 mm, 22 mm, 20 mm, 19 mm, 18 mm, 17 mm, 16 mm and 15 mm without kinking. The advantage of the bent fibrils in the composite construction was apparent. It is anticipated that further refinement of bending properties is possible.

EXAMPLE 4

An example was made similarly to Example 1, except that the outer ePTFE tube was replaced with a thinner ePTFE film tube made by helically wrapping two layers of a strip of ePTFE film (about 2.5 cm width, 50 micron fibril length, 0.01 mm thickness and 0.3 g/cc density) about the surface of a 10 mm diameter mandrel. The film was applied in a "bias-ply" fashion by helically wrapping first in one direction, then returning, back over the first wrap. The pitch of the helical wrap resulted in adjacent edges of the helical wrap being about 2.5 mm apart as measured in the direction of the tube length. The film-wrapped mandrel was heated for 10 minutes in an air convention oven set at 370° C., removed from the oven and allowed to cool. After cooling, the helically-wrapped film tube was removed from the mandrel.

The film tube was carefully fitted over the outer surface of the adhesive-coated, tensioned silicone tube. Tension was applied to the ends of the film tube, causing it to neck down in diameter and conform to the outer surface of the underlying adhesive-coated silicone tube. The outer surface of this assembly was then temporarily helically wrapped with another layer of ePTFE film and set aside overnight to cure. Following curing, the temporary outer film wrap was removed. The ends of the graft were trimmed transversely as described above and the graft removed from the mandrel.

The resulting graft had a wall thickness of about 0.8 mm. When subjected to the dialysis needle cannulation test, the graft demonstrated a leakage of about 50 ml/minute. The graft showed good bending properties and offered longitudinal stretch.

EXAMPLE 5

An example was made as described for Example 1 with the difference that both ePTFE tubes were thinner, having a wall thickness of about 0.1 mm. At the end of the construction process, while the assembled graft was still on the mandrel, the outer surface was provided with indicia along its length marking length intervals of 1.0 cm. Following curing of the elastomeric adhesive and removal of the finished graft from the mandrel and transverse trimming of the graft ends, the distance between the indicia was again measured. This distance, without any tension on the graft (i.e., in a relaxed state), was about 5.5 mm.

The resulting graft had a wall thickness of about 0.6 mm. When subjected to the dialysis needle cannulation test, the graft demonstrated a leakage of about 10 ml/minute. The graft showed good bending properties and offered longitudinal stretch.

EXAMPLE 6

An example was made as described for Example 4 with the difference that the inner ePTFE tube was thinner, having a wall thickness of about 0.1 mm. At the end of the construction process, while the assembled graft was still on the mandrel, the outer surface was provided with indicia along its length marking length intervals of 10 mm. Following curing of the elastomeric adhesive and removal of the finished graft from the mandrel and transverse trimming of the graft ends, the distance between the indicia was again measured. This distance, without any tension on the graft (i.e., in a relaxed state), was about 5.5 mm.

The resulting graft had a wall thickness of about 0.4 mm. When subjected to the dialysis needle cannulation test, the graft demonstrated a leakage of about 28 ml/minute. The graft showed good bending properties and offered longitudinal stretch.

EXAMPLE 7

An example was made generally as described by Example 3 except that, prior to fitting the silicone tube over the adhesive-coated inner ePTFE tube, a braided nitinol wire tube was fitted over the inner ePTFE tube. No outer ePTFE tube was provided, leaving the silicone tube as the outer tube. The braided wire tube was made of 0.1 mm diameter nitinol wire (Part No. SE 508, NDC, Inc., Fremont, Calif.). Braiding was accomplished on a conventional machine for making tubular braids (Steeger USA, Inc., Spartanburg, S.C.), using 32 individual strands of this wire with a braid density of about 16 picks per cm.

It was apparent that this sample could have optionally been provided with an outer ePTFE tubular covering.

The resulting graft had a wall thickness of about 0.8 mm. When subjected to the dialysis needle cannulation test, the graft demonstrated zero leakage. The graft showed good bending properties and offered longitudinal stretch.

FIGS. 7A-10 are scanning electron photomicrographs (50×) of longitudinal cross sections of cannulation sites of various tubular vascular grafts. All of the grafts shown in these photomicrographs were cannulated by the same person while the grafts were pressurized with water at room temperature as described above for testing of the various examples. The dialysis needles were of 1.5 mm diameter and were of the same type as described above for testing of the examples. Dialysis needles were used for a maximum of two punctures and then discarded. Cannulation was performed by the same technique described above for the examples.

Figure 7A:
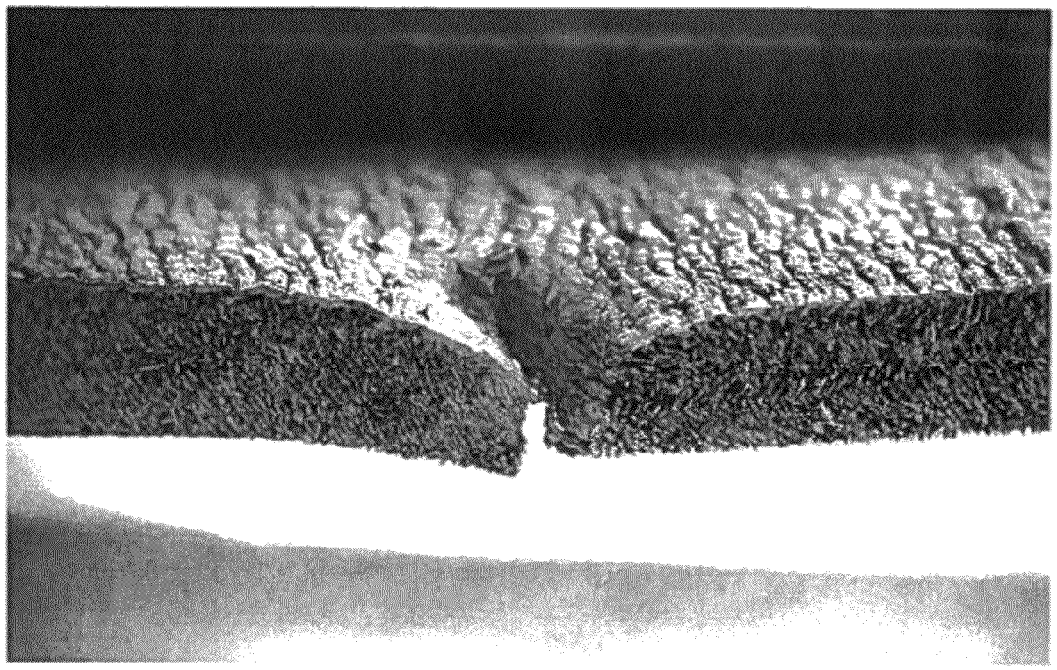
FIGS. 7A and 7B are scanning electron photomicrographs (50×) showing a longitudinal cross section of a cannulation site of a commercially available tubular graft of the prior art.
Figure 7B:
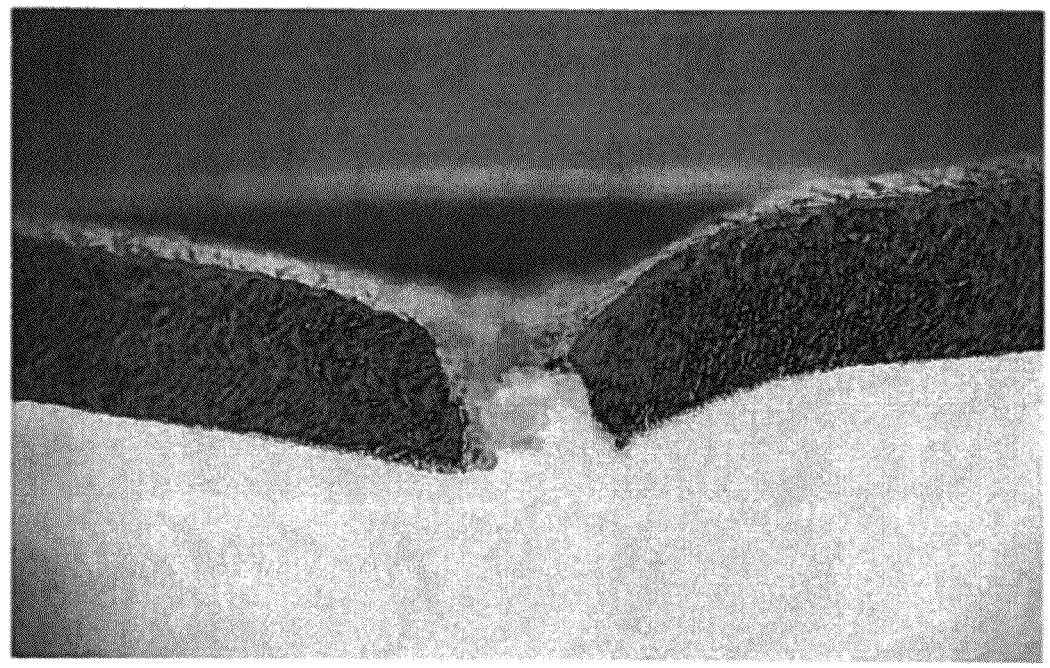
Figure 8:
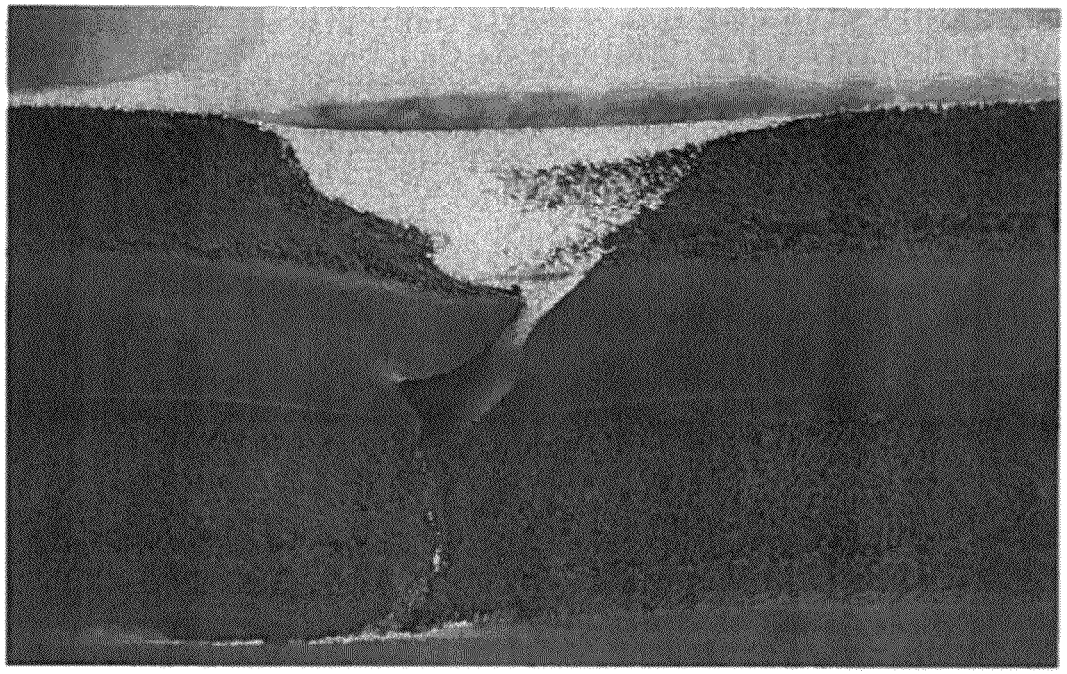
FIGS. 8, 9 and 10 are scanning electron photomicrographs (50×) of longitudinal cross sections of cannulation sites of different embodiments of tubular grafts of the present invention.
Figure 9:
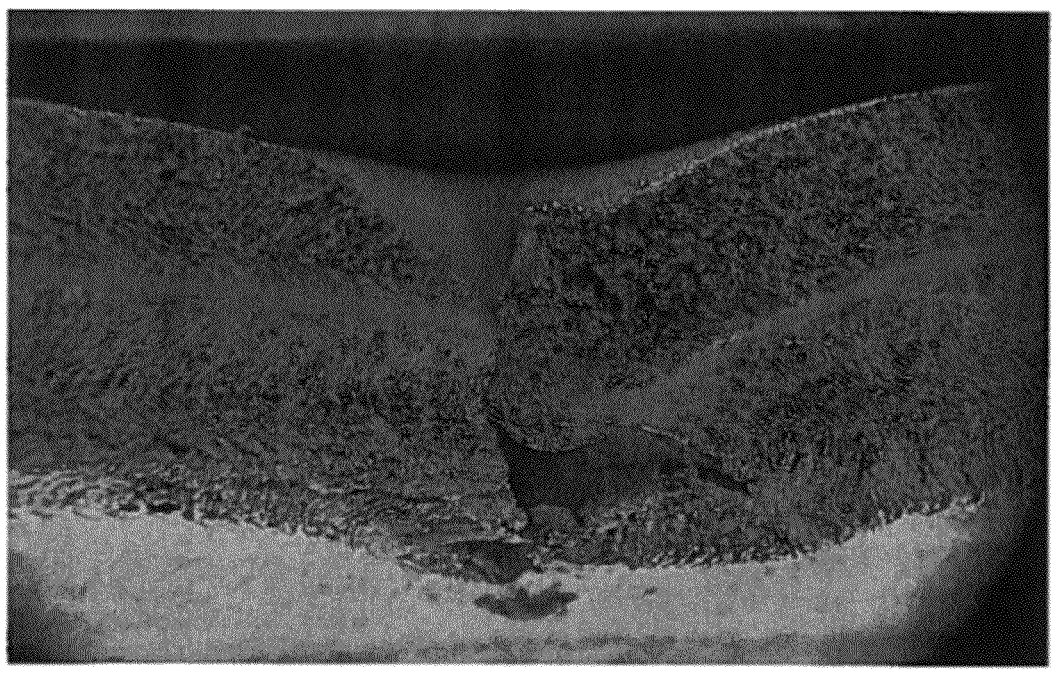
Figure 10:

FIGS. 7A and 7B are scanning electron photomicrographs of a longitudinal cross section through the same cannulation site of a commercially available graft of the prior art, a 6 mm GORE-TEX® Stretch Thin Wall Vascular Graft. While the cannulation of this sample resulted in a relatively small remaining hole through the graft wall following removal of the dialysis needle, as seen in the photomicrograph, the width of the hole was still significant (appearing to be greater than about 200 microns, in comparison to the 1500 micron needle diameter). FIGS. 8, 9 and 10 are photomicrographs of longitudinal cross sections of cannulation sites of embodiments of grafts of the present invention made, respectively, as described above by Examples 1, 3 and 5. It is seen that, following removal of the dialysis needle, the resulting aperture appears closed. As described previously, all of these grafts displayed low leakage when tested while simultaneously offering good handling properties to a surgeon.

While the principles of the invention have been made clear in the illustrative embodiments set forth herein, it will be evident to those skilled in the art to make various modifications to the structure, arrangement, proportion, elements, materials and components used in the practice of the invention. To the extent that these various modifications do not depart from the spirit and scope of the appended claims, they are intended to be encompassed therein.

The invention claimed is:

1. A method of making a tubular implantable device comprising:
    a) providing first and second expanded polytetrafluoroethylene tubes, said tubes having outer surfaces;
    b) fitting said first expanded polytetrafluoroethylene tube over a mandrel;
    c) coating at least a portion of the outer surface of said first tube with an elastomeric material;
    d) fitting said second expanded polytetrafluoroethylene tube over the coated surface of said first tube;
    e) longitudinally compressing said first and second expanded polytetrafluoroethylene tubes;
    f) curing said elastomeric material; and
    g) removing said first and second tubes from said mandrel.

2. A method of making a tubular implantable device comprising:
    a) providing first and second tubes of expanded polytetrafluoroethylene, said tubes having outer surfaces;
    b) providing an elastomeric tube having an outer surface;
    c) fitting said first tube of expanded polytetrafluoroethylene over a mandrel;
    d) coating at least a portion of the outer surface of said first tube with an elastomeric material;
    e) fitting said elastomeric tube over the first expanded polytetrafluoroethylene tube;
    f) applying tension longitudinally to said elastomeric tube and restraining both ends of said elastomeric tube to maintain said elastomeric tube in a state of tension;
    g) coating at least a portion of the outer surface of said elastomeric tube with an elastomeric material;
    h) fitting said second expanded polytetrafluoroethylene tube over the coated surface of said elastomeric tube while said elastomeric tube remains in a state of tension;
    i) curing said elastomeric material; and
    j) removing all three tubes from said mandrel wherein the tension on the elastomeric tube is released resulting in the application of axial compression to the first and second expanded polytetrafluoroethylene tubes, and trimming both ends of the resulting tubular implantable device.

* * * * *